US011855337B2

(12) United States Patent
Landherr et al.

(10) Patent No.: US 11,855,337 B2
(45) Date of Patent: Dec. 26, 2023

(54) CAPACITIVELY LOADED IMPLANTABLE LOOP ANTENNA

(71) Applicant: Cardiac Pacemakers, Inc., St. Paul, MN (US)

(72) Inventors: Daniel Joseph Landherr, Wyoming, MN (US); Niharika Varanasi, Shoreview, MN (US); John E. Hansen, Ham Lake, MN (US); Keith R. Maile, New Brighton, MN (US); Benjamin J. Haasl, Forest Lake, MN (US); Jason Lahr, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 194 days.

(21) Appl. No.: 17/016,125

(22) Filed: Sep. 9, 2020

(65) Prior Publication Data

US 2021/0083370 A1    Mar. 18, 2021

Related U.S. Application Data

(60) Provisional application No. 62/983,112, filed on Feb. 28, 2020, provisional application No. 62/900,029, filed on Sep. 13, 2019.

(51) Int. Cl.
| | |
|---|---|
| *H01Q 1/27* | (2006.01) |
| *H01Q 1/48* | (2006.01) |
| *H01Q 7/00* | (2006.01) |
| *H04Q 9/00* | (2006.01) |
| *A61N 1/372* | (2006.01) |

(52) U.S. Cl.
CPC ......... *H01Q 1/273* (2013.01); *A61N 1/37229* (2013.01); *H01Q 1/48* (2013.01); *H01Q 7/00* (2013.01); *H04Q 9/00* (2013.01); *H04Q 2213/003* (2013.01)

(58) Field of Classification Search
CPC . H01Q 1/273; H01Q 1/48; H01Q 7/00; A61N 1/37229; A61N 1/3752; H04Q 9/00; H04Q 2213/003; H04Q 2209/43
See application file for complete search history.

(56) References Cited

U.S. PATENT DOCUMENTS

| 7,047,076 B1 | 5/2006 | Li et al. |
| 7,903,043 B2 | 3/2011 | Rawat et al. |

(Continued)

OTHER PUBLICATIONS

De Vita, Placido, "Antenna selection guidelines", AN4190 Application Note, www.st.com, Doc ID 023812 Rev 1, Nov. 2012, 29 pgs.

*Primary Examiner* — Hai V Tran
*Assistant Examiner* — Michael M Bouizza
(74) *Attorney, Agent, or Firm* — Schwegman Lundberg & Woessner, P.A.

(57) ABSTRACT

A capacitively loaded loop antenna for an implantable medical device is disclosed comprising a feed extending from a conductive surface of an implantable housing, a radiating element having a cross section larger than the feed, and a return coupling the radiating element to a conductive surface of the implantable housing. The radiating element can have a height above the top surface of the implantable housing, creating a capacitance between the radiating element and the conductive surface of the implantable housing configured to counteract the inductance of the capacitively loaded loop antenna.

20 Claims, 7 Drawing Sheets

(56) References Cited

U.S. PATENT DOCUMENTS

| | | | |
|---|---|---|---|
| 8,565,891 B2 | 10/2013 | Mumbru et al. | |
| 2005/0134520 A1* | 6/2005 | Rawat | H01Q 9/42 343/873 |
| 2010/0019985 A1 | 1/2010 | Bashyam et al. | |
| 2017/0065207 A1 | 3/2017 | Landherr et al. | |
| 2018/0069303 A1* | 3/2018 | Li | H01Q 9/0421 |
| 2018/0361162 A1 | 12/2018 | Ternes et al. | |

* cited by examiner

CAPACITIVELY LOADED IMPLANTABLE LOOP ANTENNA

CLAIM OF PRIORITY

This application claims the benefit of priority under 35 U.S.C. § 119(e) of U.S. Provisional Patent Application Ser. No. 62/983,112, filed on Feb. 28, 2020, and U.S. Provisional Patent Application Ser. No. 62/900,029, filed on Sep. 13, 2019, each of which is herein incorporated by reference in its entirety.

TECHNICAL FIELD

This document relates generally to implantable medical devices, and more particularly, but not by way of limitation, to a capacitively loaded loop antenna for an implantable medical device.

BACKGROUND

Medical devices can be implanted or implantable in a body of a patient, such as to monitor patients, including detecting or sensing physiologic information from the patient and, in certain examples, provide therapy to the patient in clinical and ambulatory settings. Implantable medical devices (IMDs) can include cardiac rhythm management (CRM) devices, such as pacemakers, cardiac resynchronization devices, cardioverters, defibrillators, drug delivery devices, or one or more other IMDs implanted or implantable within a body of, or subcutaneously to, a patient. IMDs can include one or more antennae and associated telemetry circuitry configured to enable communication, such as via a radio frequency telemetry link, between the IMD and one or more external devices, such as an external programmer, located outside the body of the patient.

Traditional implantable wireless communication between an IMD and an external device consisted of near-field, non-radiative magnetic inductive coupling between the IMD and an external component, such as using a wand or other component configured to be placed over or in close proximity (on the scale of a few inches) to the IMD, as near-field losses diminish rapidly, with the near-field signal essentially vanishing within a few wavelengths from the radiating part of the antenna.

Far-field, radio frequency (RP) communication ensued to optimize far-field, radiative coupling between the IMD and an external device. All antennae have near- and far-field components. However, the size of the IMD, materials for use therewith, and the desired transmission frequency, communication range, power, and efficiency requirements will typically dictate which of the near- or far-field components are utilized for communication.

Antennae can be characterized as electromagnetically short or long depending on the physical length of the antenna with respect to the radiation frequency. Electromagnetically short antennae, shorter than half of the wavelength ($\lambda$) of the radiation frequency, have defined near- and far-field regions with respect to the wavelength of the radiation frequency (f). The near-field region is within one wavelength of the radiation frequency away from the radiating part of the antenna, including a reactive zone within $\lambda/2\pi$ (0.159 wavelengths) and a radiative zone between the reactive zone and one wavelength. The far-field region is a radiative zone greater than 2 wavelengths away from the radiating part of the antenna. For example, a communication frequency of 2.4 GHz has a wavelength in free space of 12.5 cm. Thus, at a communication frequency of 2.4 GHz, an antenna shorter than 6.25 cm in free space will behave as an electromagnetically short antenna with a far-field region greater than 25 cm from the radiating part of the antenna. There is a transition zone between the near- and far-field regions where both near- and far-field behaviors may be important. At the communication frequency of 2.4 GHz, the transition zone is between 12.5 and 25 cm in free space.

Energy is stored in the reactive zone without net energy outflow unless a load is present in the field, coupled to the radiating element inductively or capacitively. In contrast, in the radiating zone, energy is carried away from the radiating element by a radiating field regardless of the presence of a load in the field and appears to a circuit driving the radiating element as a resistive impedance, or a radiation resistance.

Electromagnetically long antennae, longer than half of the wavelength of the radiation frequency, have stronger near-field regions than electromagnetically short antennae, varying with respect to the largest dimension (D) of the radiating part of the antenna (typically a diameter, such as of a coil, dish, or other radiating element). The limit between near- and far-field regions of electromagnetically long antennae is defined by the relationship $2D^2/\lambda$, where D is the largest dimension of the radiating part of the antenna.

Other electrical characteristics can affect the transmission characteristics of an antenna, such as the medium immediately surrounding the antenna, the medium through which the radiating field propagates, and the electrical characteristics of the radiating element, the circuit driving the radiating element, and the corresponding electrical characteristics of the load, etc.

SUMMARY

This document discusses, among other things, systems and methods to enable radio frequency communication between an implantable medical device and a device separate from the implantable medical device using a capacitively loaded loop antenna comprising a feed extending from a conductive surface of an implantable housing, a radiating element having a cross section larger than the feed, and a return coupling the radiating element to a conductive surface of the implantable housing. The radiating element can have a height above the top surface of the implantable housing, creating a capacitance between the radiating element and the conductive surface of the implantable housing configured to counteract the inductance of the capacitively loaded loop antenna.

In Example 1, subject matter (e.g., an implantable medical device) may comprise: an implantable housing comprising a conductive surface; a header coupled to an outer surface of the implantable housing; control circuitry within the implantable housing, the control circuitry including a telemetry circuit configured to enable radio frequency communication with an external device separate from the implantable medical device; and a capacitively loaded loop antenna disposed within the header and coupled to the telemetry circuit, the capacitively loaded loop antenna configured to facilitate radio frequency communication comprising a feed, a radiating element, and a return to the conductive surface of the implantable housing, creating an inductance between the feed and the conductive surface. The feed may extend from the conductive surface of the implantable housing, coupling the telemetry circuit to the radiating element through a connector block. The radiating element may comprise a conductor having a larger cross section than the feed and the return, creating a capacitance between the radiating element and the conductive surface, wherein the capacitance of the radiating element is configured to counteract the inductance of the capacitively loaded loop antenna. The return may extend to the conductive surface of the implantable housing, coupling the radiating element to the conductive surface of the implantable housing, wherein the conductive surface of the implantable housing functions as a ground plane for the capacitively loaded loop antenna.

In Example 2, the subject matter of Example 1 may optionally be configured such that the telemetry circuit and the capacitively loaded loop antenna are configured to communicate at a desired communication frequency between 2.4 and 2.48 GHz when implanted in the body.

In Example 3, the subject matter of any one or more of Examples 1-2 may optionally be configured such that the capacitively loaded loop antenna has a radiation resistance between 25 and 100 ohms.

In Example 4, the subject matter of any one or more of Example 1-3 may optionally be configured such that the capacitively loaded loop antenna is a 50-ohm antenna.

In Example 5, the subject matter of any one or more of Example 1-4 may optionally be configured such that the capacitance of the radiating element is configured to cancel the inductance of the capacitively loaded loop antenna.

In Example 6, the subject matter of any one or more of Example 1-5 may optionally be configured such that the distance between the feed and the return is selected to provide a radiation resistance of the capacitively loaded loop antenna between 25 and 100 ohms.

In Example 7, the subject matter of any one or more of Example 1-6 may optionally be configured such that the radiating element has a resonating frequency in the header between 2.4 and 2.48 GIL when implanted in the body.

In Example 8, the subject matter of any one or more of Example 1-7 may optionally be configured such that the feed extends normal to the conductive surface of the implantable housing, the radiating element comprises a planar conductor having a height above the top surface of the implantable housing, a length and width along a top surface of the implantable housing, and a thickness normal to the top surface of the implantable housing, and the return extends normal to the conductive surface of the implantable housing.

In Example 9, the subject matter of any one or more of Example 1-8 may optionally be configured such that the length, width, and thickness of the radiating element in the header is selected to resonate at a communication frequency between 2.4 and 2.48 GHz when implanted in the body.

In Example 10, the subject matter of any one or more of Example 1-9 may optionally be configured such that the length of the radiating element is between 5 and 8 mm, the width of the radiating element is between 1 and 2.5 mm, and the thickness of the radiating element is between 0.2 and 0.6 mm.

In Example 11, the subject matter of any one or more of Example 1-10 may optionally be configured such that the height of the radiating element above the top surface of the implantable housing is between 7 and 11 mm.

In Example 12, the subject matter of any one or more of Example 1-11 may optionally be configured such that the radiating element has a length along the top surface of the implantable housing, and the height of the radiating element above the top surface of the implantable housing is greater than the length of the radiating element.

In Example 13, the subject matter of any one or more of Example 1-12 may optionally be configured such that the radiating element has a length and width along the top surface of the implantable housing, the length of the radiating element is greater than the width, and the height of the radiating element above the top surface of the implantable housing is greater than the length of the radiating element.

In Example 14, the subject matter of any one or more of Example 1-13 may optionally be configured such that the radiating element is parallel to the top surface of the implantable housing.

In Example 15, the subject matter of any one or more of Example 1-14 may optionally be configured such that the header is composed of a material having a dielectric constant between 2 and 5, and the header is configured to electrically isolate the capacitively loaded loop antenna from tissue of a patient when implanted.

In Example 16, subject matter (e.g., an implantable medical device) may comprise: an implantable housing comprising a conductive surface; a header coupled to an outer surface of the implantable housing; control circuitry within the implantable housing, the control circuitry including a telemetry circuit configured to enable radio frequency communication with an external device separate from the implantable medical device; and a capacitively loaded loop antenna disposed within the header and coupled to the telemetry circuit, the capacitively loaded loop antenna configured to facilitate communication at a communication frequency between 2.4 and 2.48 GHz when implanted in the body, the capacitively loaded loop antenna comprising a feed, a radiating element, and a return to the conductive surface of the implantable housing, creating an inductance between the feed and the conductive surface. The feed may extend normal to the conductive surface of the implantable housing, coupling the telemetry circuit to the radiating element through a connector block. The radiating element may comprise a planar conductor having a length and width parallel to a portion of a top surface of the implantable housing, a thickness normal to the top surface of the implantable housing, and a height above the top surface of the implantable housing, creating a capacitance between the radiating element and the conductive surface, wherein the capacitance of the radiating element is configured to counteract the inductance of the capacitively loaded loop antenna. The return may extend normal to the conductive surface of the implantable housing, coupling the radiating element to the conductive surface of the implantable housing, wherein the conductive surface of the implantable housing functions as a ground plane for the capacitively loaded loop antenna.

In Example 17, the subject matter of Example 1 may optionally be configured such that the radiating element has a resonating frequency in the header between 2.4 and 2.48 GHz when implanted in the body, and the header is composed of a material having a dielectric constant between 2 and 5.

In Example 18, the subject matter of any one or more of Example 16-17 may optionally be configured such that the length of the radiating element is between 5 and 8 mm, the width of the radiating element is between 1 and 2.5 mm, the thickness of the radiating element is between 0.2 and 0.6 mm, the height of the radiating element above the top surface of the implantable housing is between 7 and 11 mm, and the capacitively loaded loop antenna has a radiation resistance between 25 and 100 ohms.

In Example 19, the subject matter of any one or more of Example 16-18 may optionally be configured such that the length of the radiating element is 7.1 mm, the width of the radiating element is 1.5 mm, the thickness of the radiating element is 0.4 mm, and the height of the radiating element above the top surface of the implantable housing is 8.3 mm.

In Example 20, the subject matter of any one or more of Example 16-19 may optionally be configured such that the length of the radiating element is 5.7 mm, the width of the radiating element is 1.75 mm, the thickness of the radiating element is 0.4 mm, and the height of the radiating element above the top surface of the implantable housing is 9.6 mm.

In Example 21, subject matter (e.g., an implantable medical device) may comprise: an implantable housing comprising a conductive surface; a header coupled to an outer surface of the implantable housing; control circuitry within the implantable housing, the control circuitry including a telemetry circuit configured to enable radio frequency communication with an external device separate from the implantable medical device; and a capacitively loaded loop antenna disposed within the header and coupled to the telemetry circuit, the capacitively loaded loop antenna configured to facilitate radio frequency communication comprising a feed, a radiating element, and a return to the conductive surface of the implantable housing, creating an inductance between the feed and the conductive surface. The feed may extend from the conductive surface of the implantable housing, coupling the telemetry circuit to the radiating element through a connector block. The radiating element may comprise a conductor having a larger cross section than the feed and the return, creating a capacitance between the radiating element and the conductive surface, wherein the capacitance of the radiating element is configured to counteract the inductance of the capacitively loaded loop antenna. The return may extend from the radiating element to the conductive surface of the implantable housing, coupling the radiating element to the conductive surface of the implantable housing, wherein the conductive surface of the implantable housing functions as a ground plane for the capacitively loaded loop antenna.

In Example 22, the subject matter of any one or more of Example 1-20 may optionally be combined with Example 21.

In Example 23, subject matter (e.g., a system or apparatus) may optionally combine any portion or combination of any portion of any one or more of Examples 1-22 to comprise "means for" performing any portion of any one or more of the functions or methods of Examples 1-22, or at least one "non-transitory machine-readable medium" including instructions that, when performed by a machine, cause the machine to perform any portion of any one or more of the functions or methods of Examples 1-22.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of Which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
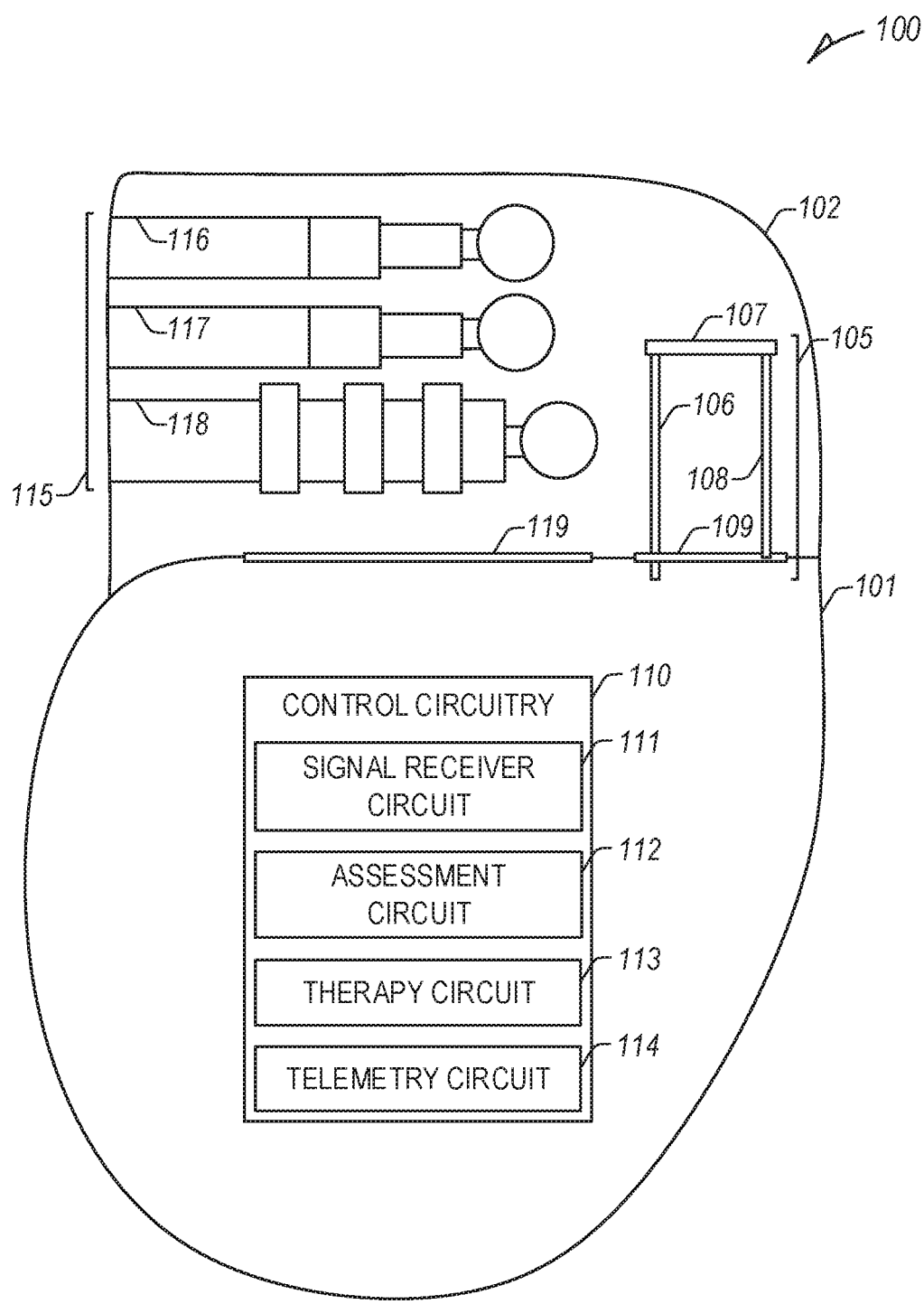
FIG. 1 illustrates an example antenna disposed in a header of an MID.

Different antennae require different physical characteristics or configurations to communicate at specific frequencies through different mediums. In contrast, the size of IMDs, and in certain examples, non-implantable AMDs, and available power for communication, can be limited, presenting communication challenges at certain radio frequencies.

The present inventors have recognized, among other things, specific antenna configurations, including physical configurations and placement with respect to an IMD, to enable communication between the IMD and an external device in the Industrial, Scientific and Medical (ISM) short-range radio band, in the 2.4-2.48 GHz frequency range, commonly referred to as the Bluetooth frequency band. Communication at such frequency range is common, and antennae exist with respect to such range, however, traditional monopole designs have a relatively high radiation resistance and reactance, which are difficult to match in an implanted or implantable environment. In addition, communication from inside the body can require higher antennae gain to compensate for tissue losses in the 2.4-2.48 GHz frequency range.

The limited power and computational resources of IMDs make antennae transmission efficiency and efficiency of associated telemetry circuit especially important. In addition, the range of communication of the antenna and associated telemetry circuit must also be far enough to be usable for a patient or system in operation.

Antennae radiate most efficiently if the length of the antenna is an integral number of half-wavelengths of the driving signal. A dipole antenna, for example, is a center-driven conductor that has a length equal to half the wavelength of the driving signal. Such a dipole antenna can be made, for example, of two lengths of metal arranged end to end with the cable from a transceiver coupled to each length of the dipole in the middle. An efficiently radiating resonant structure is formed if each length of metal in the dipole is a quarter-wavelength long, so that the combined length of the dipole from end to end is a half-wavelength. A shorter antenna can produce a similar field configuration by utilizing a ground plane to reflect electromagnetic waves emitted by the antenna and thereby produce an image field. A monopole antenna includes a conductor with a length equal to one-quarter the wavelength of the driving signal situated with respect to a reflecting ground plane so that the total emitted and reflected field configuration resembles that of the dipole antenna.

By way of example, for a carrier signal of 2.4-2.48 GHz, the wavelength in free space is approximately 12.5 cm. In free space, a half-wavelength dipole antenna would optimally be approximately 6.25 cm long, and a quarter-wavelength monopole antenna would optimally have a length approximately 3.125 cm with a housing of the IMD, or other conductive surface, serving as a ground plane. Because the permittivity of body tissues is greater than that of free space, the corresponding optimum dipole and monopole antennas in the human body, or a dielectric, such as a traditional header design of an BID, would be approximately half of these lengths or less. However, space for even these lengths are not typically available in traditional header designs.

Antennae are also characterized by a quality, or Q factor, and an impedance. The Q of an antenna is a measure of performance or quality of a resonator and is a function of the measure of energy loss or dissipation per cycle as compared to the energy stored in the fields inside the resonator. Antenna impedance is the sum of a real component and an imaginary component of the antenna. In one embodiment, the antenna of the present subject matter presents an impedance between approximately 25 and 100 ohms, such as 50 ohms. However, lower or higher impedances area also contemplated.

The antenna described herein can include a conductor disposed within a header of an IMD, The antenna, in various embodiments can be insulated or uninsulated (separately from the header) and can be electrically connected to one or more telemetry circuits within the housing. The antenna includes a conductive structure capable of radiating electromagnetic energy, such as a rod, a wire, a planar conductor, etc. In one embodiment, the antenna includes a flexible or rigid conductor (e.g., ribbon, etc.) with a substantially planar shape, having a length, width, and thickness, and a height with respect to the conductive housing of the IMI). Each of these physical characteristics affect the electrical characteristics of the antenna, and accordingly, the performance of the antenna.

FIG. 1 illustrates an example IMD 100 comprising a conductive, hermetically sealed housing (CAN) 101 and a header 102. The CAN 101 can be composed of a biocompatible electrically conductive material and can include one or more control circuits of the IMD 100, such as control circuitry 110. In certain examples, the CAN 101 can provide electrical ground for the IMD 100. The header 102 can be composed of a biocompatible electrically insulative material coupled to a first edge (e.g., a top edge in the orientation of FIG. 1) of the CAN 101. The header 102 can include a first antenna 105 disposed therein, and further can include one or more lead ports 115, such as first, second, and third lead ports 116, 117, 118 configured to receive first, proximal ends of respective first, second, and third leads. When the IMD 100 is implanted, the header 102 can electrically isolate the first antenna 105 and the electrical connections of the lead ports 115 from the body. The electrical connections of the lead ports 115 can be coupled to one or more electrical circuits in the CAN 101 through a lead port connector block 119. In an example, the connector blocks described herein can enable conductive connections through an otherwise hermetically-sealed conductive CAN 101, while insulating connection from the CAN 101.

The first antenna 105 can include an inductive loop configured to concentrate current flow at the antenna, directing coupling away from the body and other header elements. The first antenna 105 can further include a capacitive element outside of the conductive housing of the CAN 101. A feed 106 connects a first end of a radiating element 107 of the first antenna 105 to one or more electrical circuits in the CAN 101 through an antenna connector block 109. The radiating element 107 can include a conductor, in certain examples, having a thickness and width greater than the feed 106. A second end of the radiating element 107 can be coupled to a return 108, such as to couple a second end of the radiating element 107 to the CAN 101, which can serve as electrical ground for the antenna 105. The overall length of the radiating element 107 (e.g., including the feed 106 as it exits the CAN 101, couples to the proximate end of the radiating element 107, to the distal end of the radiating element 107 where the radiating element 107 couples to the return 108) can be configured to be resonant at the desired radiation frequency (e.g., 2.4-2.48 GHz) when implanted in the body (the radiating element 107 will be resonant at a different frequency in free space, when not implanted), in concert with the dielectric of the header 102 (e.g., an epoxy, ceramic, resin, thermoplastic, or other electrical insulative material having a relative permittivity between 2 and 5, such as Tecothane® having a dielectric constant of 4.4, etc.), an inductance of the first antenna 105 (from the feed 106 to the return 108), and the capacitance between the radiating element 107 and the ground plane (e.g., the CAN 101).

The control circuitry 110 can include one or more of a signal receiver circuit 111, an assessment circuit 112, a therapy circuit 113, and a telemetry circuit 114. In certain examples, the IMI) 100 can include one or more other sensors, such as one or more electrodes, accelerometers, posture sensors, pressure sensors, etc. The signal receiver circuit 111 can be configured to receive physiologic information, such as from the patient through one or more of the lead ports 115, or one or more other sensors associated with the IMD 100, such as an accelerometer, a posture sensor, a CAN electrode, etc. The assessment circuit 112 can be configured to determine or measure one or more parameters, such as using information from the signal receiver circuit 111.

In an example, the assessment circuit 112 can provide a first level or amount of processing of received physiologic information. However, the desired computational resources and power requirements of the POD 100 can limit the amount of desired computation that can be done in an implantable setting without adversely affecting longevity, cost, or performance of the IMD 100. A second, higher level of processing requiring more computational resources and power can be accomplished using one or more external devices outside of the body, such as to ease the computational resources or power burden of the assessment circuit 112 or the MID 100. In an example, one or more external devices can determine one or more therapy or other parameters to program or control the IMD 100.

The therapy circuit 113 can include a pulse generator or electrical circuitry configured to provide electrostimulation therapy to electrically stimulate a heart or other excitable tissue of a patient, such as to help restore or improve cardiac performance or provide one or more other therapies to the patient. In certain examples, electrostimulation therapy can include cardiac resynchronization therapy (CRT), such as biventricular (BiV) pacing, synchronized left ventricle (LV)-only pacing, etc. CRT can improve heart pumping efficiency and increase blood flow in some heart failure patients, decreasing hospitalization and morbidity associated with heart failure or worsening heart failure (\VHF), as well as improving patient quality of life (QoL). Stimulation parameters can include a selection of stimulation type, one or more stimulation sites, one or more stimulation electrodes or vectors, or one or more other parameters, such as an atrio-ventricular delay (AVD) interval, a stimulation energy, etc. In certain examples, stimulation parameters can be selected using timing information from one or more cardiac electrical features or parameters (e.g., a P wave, a Q wave, an R wave, a QRS complex, a T wave, etc.) and one or more other cardiac electrical or mechanical features (e.g., LV activation, RV activation, etc.), such as a Q-LV interval, etc., or timings of one or more other cardiac electrical parameters (e.g., RV-LV interval, etc.), such as disclosed in the commonly assigned Ternes et al. U.S. patent application Ser. No. 16/007,094, titled "Systems and Methods for Dynamic Control of Heart Failure Therapy", herein incorporated by reference in its entirety.

The telemetry circuit 114 can include one or more transmitter circuits configured to prepare and send information from the IMD 100, such as the information received by the signal receiver circuit 111 or determined or measured by the assessment circuit 112, or one or more other IMD 100 parameters, such as operation or device information, etc., to one or more external devices (e.g., a medical device programmer, etc.) using the first antenna 105. Further, the telemetry circuit 114 can include one or more receiver circuits configured to receive, through the first antenna 105, information from one or more other devices, such as an external device, another IMD, one or more ambulatory medical devices (AMD), etc.

Figures 2A, 2B:
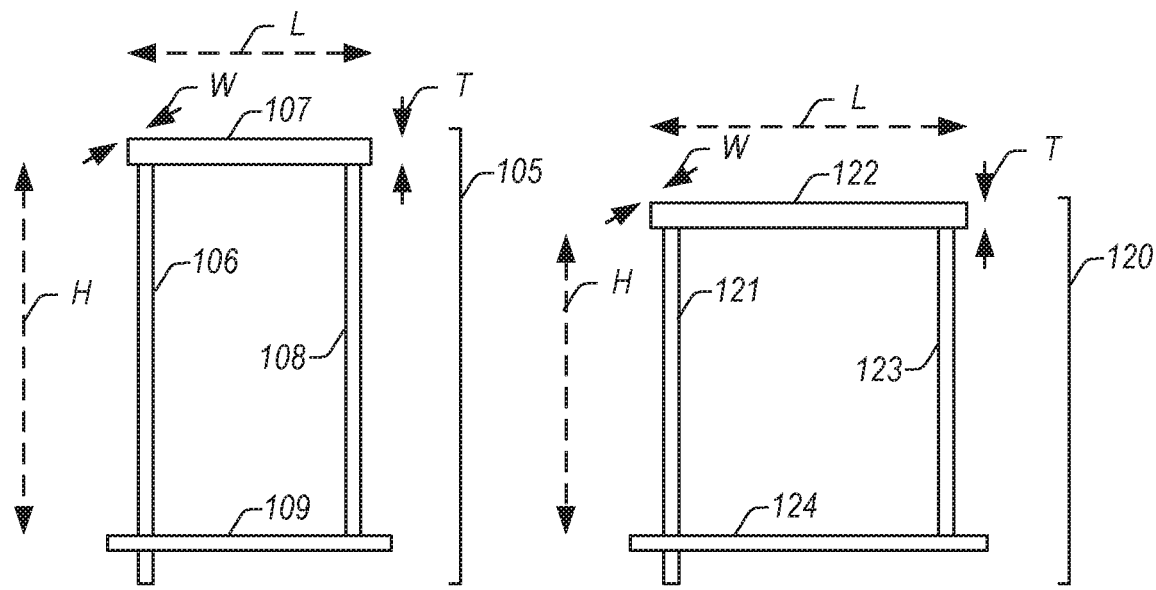
FIGS. 2A-2B illustrate example antennae configurations.

FIGS. 2A-2B illustrate example antennae configurations, including the first antenna 105 of FIG. 1 and a second antenna 120. In FIG. 2A, the first antenna 105 includes a feed 106, a radiating element 107, a return 108, and an antenna connector block 109. In an example, the radiating element 107 can be a planar conductor having a length (L), a width (W), a thickness (T), and a height (H) above the corresponding ground plane (e.g., the surface of the CAN). The radiating element 107 can be rigid or flexible, taking a specific two- or three-dimensional shape. In certain examples, the radiating element 107 can include a smooth conductor, as a rough finish can cause losses at the desired communication frequency.

The antenna 105 creates a loop between the feed 106 and ground (e.g., the surface of the CAN) through the return 108, the loop having an inductance. In addition, the interaction between the radiating element 107 and the ground plane (e.g., the surface of the CAN) creates a capacitance, controlled by the height of the radiating element 107 from the ground plane. The shape of the radiating element 107 (e.g., the length and in certain examples, the width or thickness) further impacts the efficiency of the antenna 105 at the desired communication frequency. Further, the distance between the feed 106 (e.g., as it exits the CAN 101) and the return 108 (e.g., at the point it connects to the ground plane) impacts the radiation resistance. In an example, the total distance of the first antenna 105 outside of the CAN 101 contributes to the radiation resistance. Each of these variables can be controlled to optimize the efficiency of the antenna at a desired communication frequency, such that the capacitance (e.g., of the radiating element 107) cancels or substantially counteracts (e.g., reduces the electrical effect of, such as 5 ohms or less) the inductance of the first antenna 105 at the desired communication frequency, while providing a radiation resistance between 25 and 100 ohms (e.g., 50 ohms) to optimize power handling and signal losses, and to match the remaining communication elements (e.g., a matching antenna and telemetry circuit), to optimize efficiency of communication at the desired communication frequency. In certain examples, optimizing physical elements of the antenna can increase the bandwidth at the resonant frequency, reduce losses, or reduce the amount of matching circuits required by corresponding telemetry circuits.

As an example, at the desired communication frequency of 2.4 GHz (e.g., between 2.4-2.48 GHz) when implanted in the body, the antenna 105 can have the following dimensions: height (H) of 9.6 mm; length (L) of 5.7 mm; width (W) of 1.75 mm; and thickness (T) of 0.4 mm. Here, the distance between the feed 106 and the return 108 is similarly 5.7 mm, as the feed 106 and the return 108 are substantially normal to the ground plane (e.g., the surface of the CAN), and the radiating element 107 is substantially parallel to the ground plane. In other examples, other combinations of dimensions can be used to communicate at the desired communication frequency of 2.4 GHz when implanted in the body, such as illustrated in FIG. 2B.

FIG. 2B illustrates the second antenna 120, similar to the first antenna 105, but with different dimensions. The second antenna 120 includes a feed 121, a radiating element 122, a return 123, and an antenna connector block 124. The second antenna 120 is shorter than the first antenna 105 with respect to the ground plane, but has a longer and narrower radiating element 122, while still providing a capacitance that cancels or substantially counteracts the inductance of the second antenna 120 at the desired communication frequency; while providing a radiation resistance between 25 and 100 ohms (e.g., 50 ohms).

As an example, at the desired communication frequency of 2.4 GHz (e.g., between 2.4-2.48 GHz) when implanted in the body, the second antenna 120 can have the following dimensions: height (H) of 8.3 mm; length (L) of 7.1 mm; width (W) of 1.5 mm; and thickness (T) of 0.4 mm. Here, the distance between the feed 121 and the return 123 is similarly 7.1 mm, as the feed 121 and the return 123 are substantially normal to the ground plane (e.g., the surface of the CAN), and the radiating element 122 is substantially parallel to the ground plane.

In other examples, other dimensions can be used, such as depending on one or more other characteristics or dimensions of the IMD, proximity to one or more other conductors, etc. For example, at the desired communication frequency of 2.4 GHz when implanted in the body, the length of the antenna 120 can range between 5 and 8 mm, the width can range between 1 and 2.5 mm, the thickness can range between 0.2 and 0.6 mm, and the height can range between 7 and 11 mm, depending on one or more other IMD characteristics. As one dimension of the antenna 120 changes, the others can change accordingly. For example, so does the width, thickness, and height.

For each of the antennae of FIGS. 2A-2B, the feeds 106, 121 and returns 108, 123 include wires (e.g., smooth conductors) or other conductors having cross sections smaller than the cross section of the radiating elements 107, 122, the feeds 106, 121 and returns 108, 123 configured to be coupled (e.g., soldered or otherwise electrically attached) to the radiating elements 107, 122 (e.g., planar, conductive radiating elements) at or substantially near the proximal and distal edges of the respective radiating elements 107, 122. In an example, the conductive materials of the antennae 105; 120 are fabricated of metal, such as, for example, an alloy of platinum and iridium. In one embodiment, the alloy includes approximately 90% platinum and 10% iridium. Such material is commonly used for feedthroughs of therapeutic leads and is both mechanically strong and biocompatible. In one embodiment, the conductor includes niobium, which has a slightly lower resistivity than the 90% platinum and 10% iridium alloy. Other materials for the antennae 105, 120 are also contemplated, including, but not limited to, stainless steel, gold, silver and other biocompatible conductors having low resistance.

In other examples, other dimensions or different shapes can be provided by the different components of the antennae 105, 120 to provide different radiation resistance, capacitance, or inductance, such as to tune the antenna to match one or more other components, such as the telemetry circuitry of the MID, the electrical characteristics of the body, or one or more other antenna or corresponding telemetry circuits. In other examples, the dielectric constant of the header material can be increased to further reduce the required size of the antenna for the desired communication frequency of 2.4 GHz when implanted in the body, as well as reduce losses to the body (while increasing losses to the header material). Although illustrated herein with respect to the antennae 105, 120 in the header on a top surface of the CAN, in other examples, the antennae 105, 120 can be laced parallel or perpendicular to the main face of the CAN, placed on one or more other edge of the CAN, or one or more of the feeds 106, 121 or returns 108, 123 can include a ribbon or planar conductor, as opposed to the wire or round conductor illustrated herein. In other examples, to increase the capacitance of the antennae 105, 120 with respect to the body, instead of with respect to the CAN, the thickness of the radiating elements 107, 122 can be greater than the width of the radiating elements 107, 122.

Figure 3:
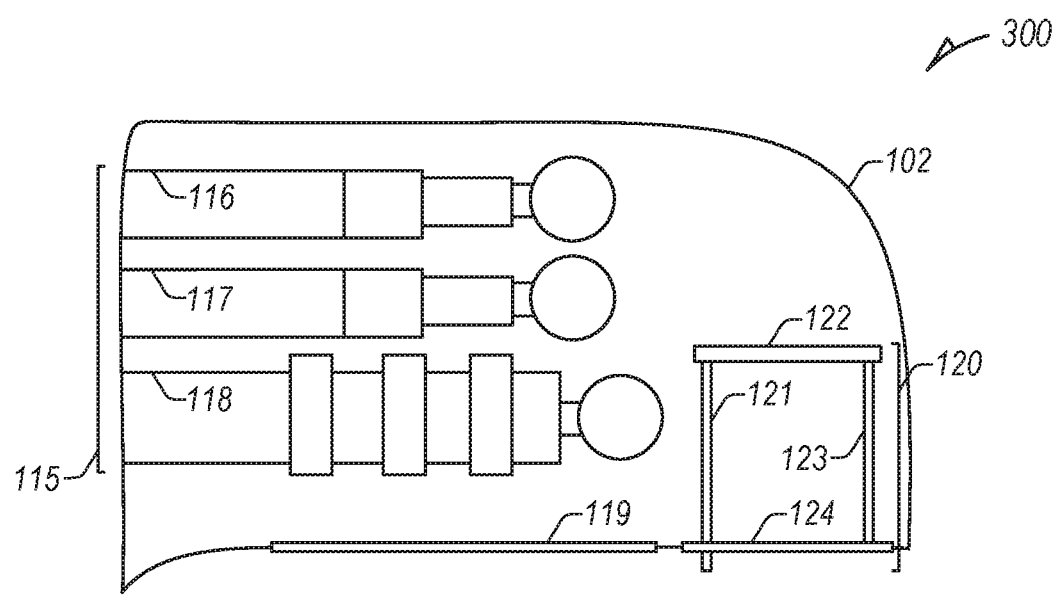
FIG. 3 illustrates an example antenna disposed in a header of an MID.

FIG. 3 illustrates the second antenna 120 of FIG. 2B in a header 102 of an IMD 300, similar to that illustrated in FIG. 1 with respect to the first antenna 105. The IMD 300 includes lead ports 115, a lead port connector block 119, and the second antenna 120 in the header 102, such as illustrated and described in FIGS. 1 and 2B.

Figure 4A:
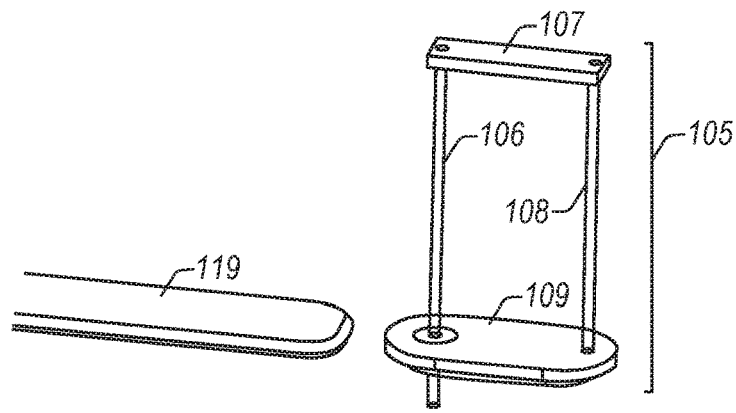
FIGS. 4A-4B illustrate example antennae configurations.
Figure 4B:
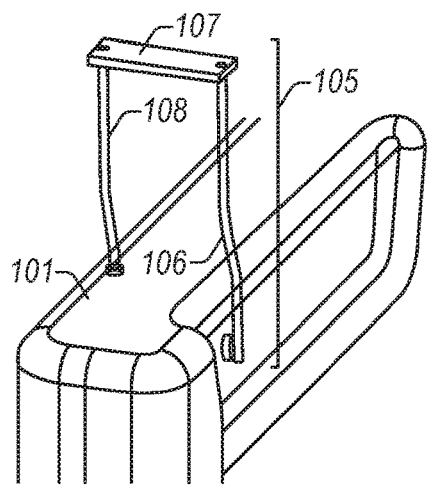

FIGS. 4A-4B illustrate perspective views of different antenna configurations. FIG. 4A illustrates a perspective view of the first antenna 105 of FIG. 1, including the feed 106, the radiating element 107, the return 108, and the antenna connector block 109, such as illustrated in FIG. 1.

FIG. 4B illustrates a perspective view of another embodiment of the first antenna 105 in a different physical configuration with respect to the CAN 101. In FIGS. 1 and 4A, the radiating element 107 of the first antenna 105 is configured along the top edge of the CAN 101. In FIG. 4B, the radiating element 107 of the first antenna 105 is perpendicular to the top edge of the CAN 101, and the feed 106 exits the side of the CAN 101 instead of the top. The feed 106 and return 108 are also curved, impacting the inductance and radiation resistance of the antenna 105. Although the width of the header of the IMD is narrower than the length, limiting the length of the radiating element 107 in this configuration, the antenna 105 is a greater distance from the remaining components in the header, such as one or more lead ports, etc., in certain examples, including conductors and electrical signals that can interfere with the radiation pattern or electrical characteristics of the antenna 105.

Figure 5:
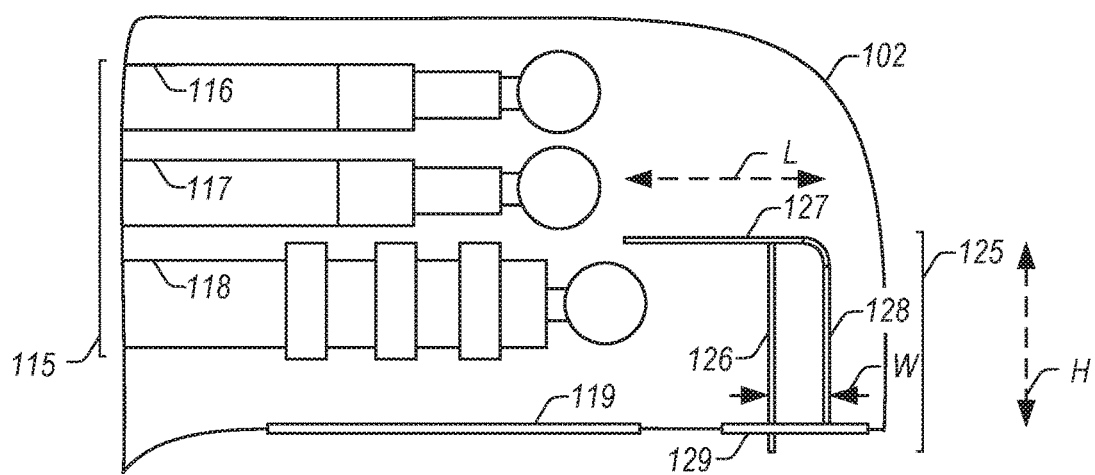
FIGS. 5-7 illustrate example antennae disposed in a header of an IMD.

FIG. 5 illustrates an example third antenna 125 in a header 102 of an IMD 500. The third antenna 125 is a wire antenna having a feed 126, a radiating element 127, a return 128, and an antenna connector block 129. The radiating element 127 of FIG. 5 is longer than the radiating element 107 of FIG. 1, such as to account for the smaller cross section volume (e.g., a combination of the width, thickness, etc.) in contrast to that of the radiating element 107 of the first antenna 105. The dimensions of the third antenna 125, including the length (L) of the radiating element 127, the width (W) between the feed 126 and the return 128, and the height (H) of the radiating element 127 with respect to a ground plane (e.g., a conductive surface of the CAN 101), can all be configured to provide a desired inductance, capacitance, and radiation resistance at the desired communication frequency, such as described above.

As an example, at the desired communication frequency of 2.4 GHz (e.g., between 2.4-2.48 GHz) when implanted in the body, the third antenna 125 can have the following dimensions: height (H) of 9 mm; length (L) of 10 mm; and a width (W) of 3 mm, as the feed 126 and the return 128 are substantially normal to the ground plane (e.g., a conductive surface of the CAN 101), and the radiating element 127 is substantially parallel to the ground plane. In other examples, one or more other configurations or dimensions can be used.

In other examples, other combinations of wire, stamped ribbon, or other shapes or configurations can be used to provide an antenna configured to resonate at the desired communication frequency. In certain examples, one or more lumped capacitive or inductive elements can be combined with one or more of the antennas described herein. For example, at least one of a capacitive or inductive element can be added between the radiating element 127 and the ground plane. In one an example, a capacitive element or an inductive element can be added to the radiating element 127 (e.g., to the distal side of the radiating element 127, opposite the proximal end of the radiating element 127 coupled to the return 128, such as between the feed 126 and the distal end of the radiating element 127), between the radiating element 127 and the ground plane. In an example, an inductive element can replace the return 128 between the radiating element 127 and the ground plane. In an example, a capacitive element can be added to between the distal end of the radiating element 127 and the ground plane, and an inductive element can replace the return 128 between the radiating element 127 and the ground plane. Similar changes can be made to the remaining configurations disclosed herein (e.g., FIGS. 1, 3, 5, etc.).

Figure 6:
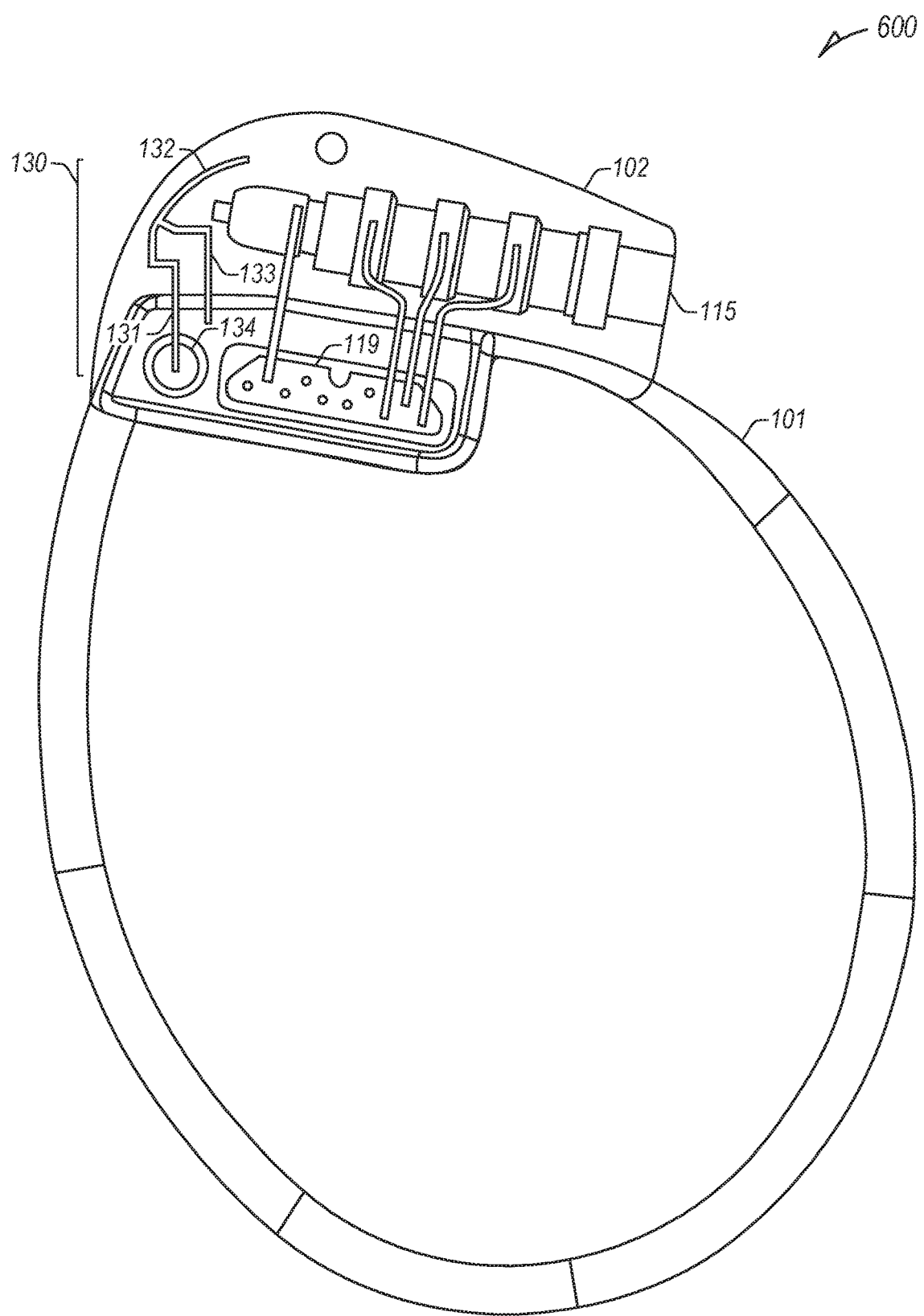
Figure 7:
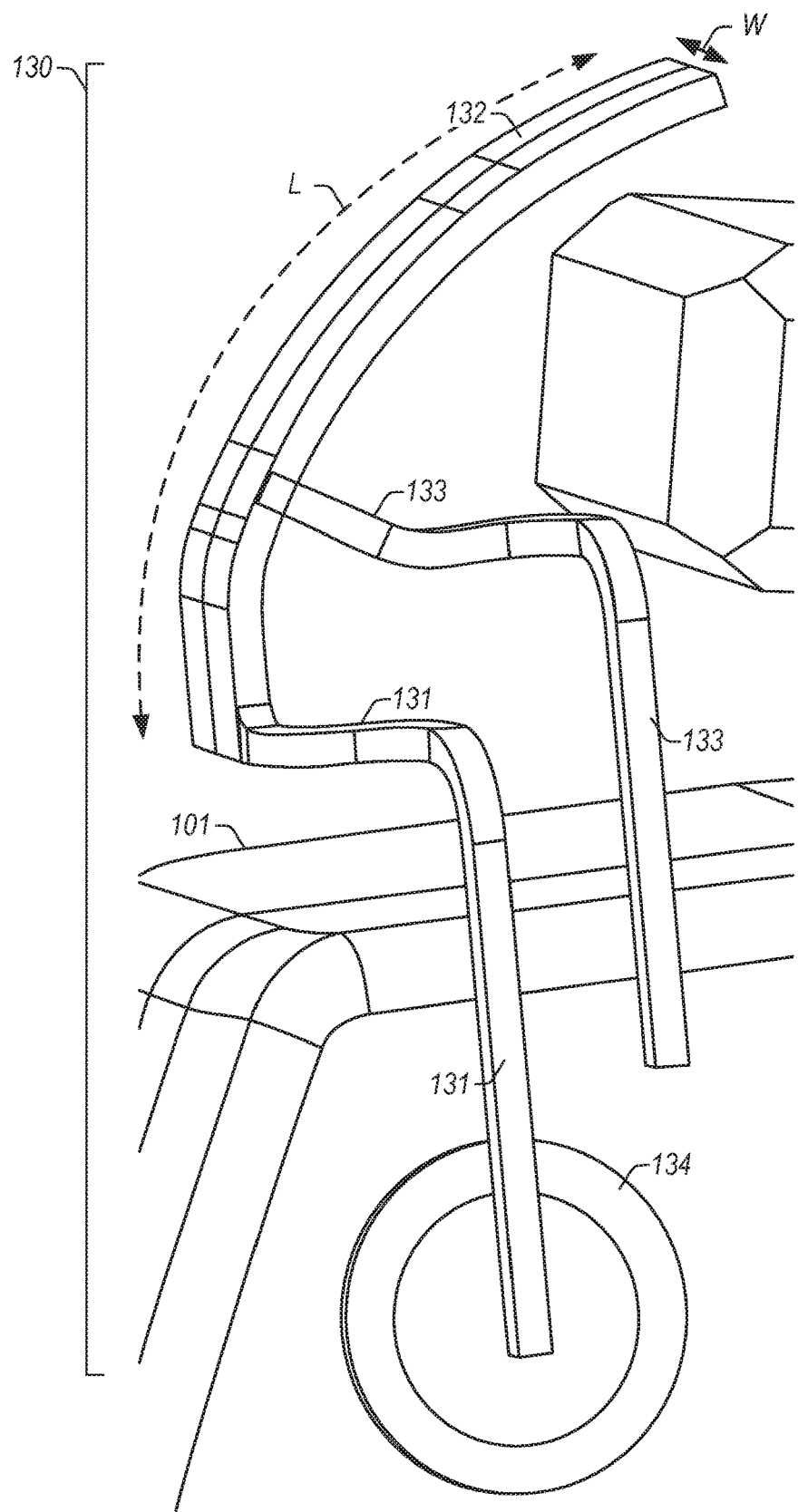

FIGS. 6-7 illustrates an example fourth antenna 130 in a header 102 of an IMD 600 including a single lead port 115 and a different shape and smaller overall volume than the headers 102 illustrated in FIGS. 1, 3, and 5. The fourth antenna 130 includes a feed 131, a radiating element 132 (e.g., a top-loaded radiating element), a return 133. The length (L) of the radiating element 132 along the outer surface of the header 102, in addition to the cross section volume (e.g., a combination of width, thickness, etc., and the relative distance between the feed 131 and the return 133 (including a placement of the return 133 along the radiating element 132), can be configured to provide a desired inductance, capacitance, and radiation resistance at the desired communication frequency, such as described above. The feed 131 can include a proximate end coupled to an antenna connector block 134 and a distal end coupled to a first end of the radiating element 132. The return 133 can include a proximate end coupled to a portion of the radiating element 132 and a distal end coupled to a ground plane (e.g., directly connected to a conductive surface of the CAN 101).

As an example, at the desired communication frequency of 2.4 GHz (e.g., between 2.4-2.48 GHz) when implanted in the body, the radiating element 132 (e.g., a top-loaded ribbon arc) can have a length (L) of approximately 10.15 mm near a rear surface of the header 102 extending from the distal end of the feed 131 along an outer surface of the header 102 (in this example, not parallel to the outer surface of the header 102) towards the top and front of the header 102. The width (W) of the radiating element 132 can be substantially larger (e.g., by at least a factor of 1.5, 2, or greater) than the thickness of the radiating element 132 or the width of the feed 131 or the return 133 (e.g., the radiating element 132 can have a width (W) of approximately 1.78 mm). In an example, the lengths of the feed 131 and the return 133 can be similar to the length of the radiating element 132 (e.g., the feed 131 can have a length of approximately 10.23 mm, the return 133 can have a length of approximately 10.65 mm, etc.). The location of the proximate end of the return 133 along the radiating element 132, such as the spacing between the distal end of the feed 131 and the proximate end of the return 133 along the radiating element 132, can impact the electrical characteristics of the fourth antenna 130, such as the radiation resistance, inductance, etc. In an example, to provide a radiation resistance of approximately 50 ohms for the fourth antenna 130 illustrated in FIGS. 6 and 7, the spacing between the distal end of the feed 131 and the proximate end of the return 133 along the radiating element 132 can be approximately 2.82 mm. In certain examples, the lengths, widths, thicknesses, and spacings above can be approximate (e.g., can vary by several percent) or can vary with the shape of the fourth antenna 130, the position of the fourth antenna 130 to one or more other conductors, the material of the header 102, etc. In other examples, one or more other configurations or dimensions can be used.

Figure 8:
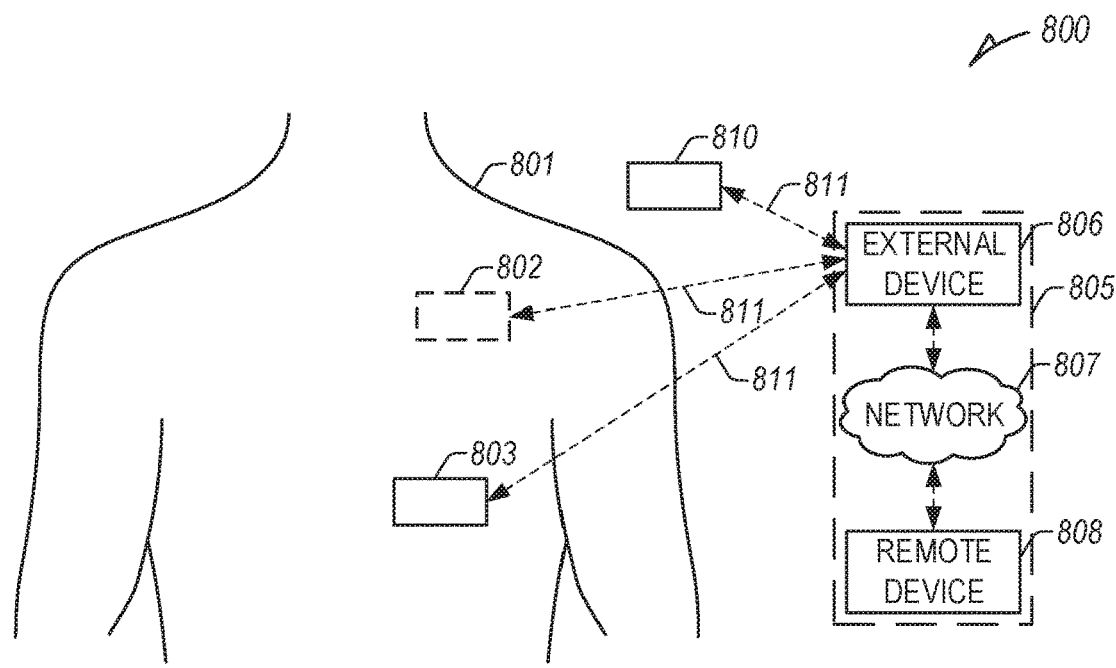
FIG. 8 illustrates an example patient management system.

FIG. 8 illustrates an example patient management system 800 and portions of an environment in which the system 800 may operate. The patient management system 800 can perform a range of activities, including remote patient monitoring and diagnosis of a disease condition. Such activities can be performed proximal to a patient 801, such as in a patient home or office, through a centralized server, such as in a hospital, clinic, or physician office, or through a remote workstation, such as a secure wireless mobile computing device.

The patient management system 800 can include one or more ambulatory devices, an external system 805, and a communication link 811 providing for communication between the one or more ambulatory devices and the external system 805, such as using one or more antennae and telemetry circuits. The one or more ambulatory devices can include an implantable medical device (MID) 802, a wearable medical device 803, or one or more other implantable, leadless, subcutaneous, external, wearable, or ambulatory medical devices configured to monitor, sense, or detect information from, determine physiologic information about, or provide one or more therapies to treat various cardiac conditions of the patient 801, such as high blood pressure, an ability of a heart to sufficiently deliver blood to a body, including atrial fibrillation (AF), congestive heart failure (CHF), hypertension, or one or more other cardiac or non-cardiac conditions (e.g., dehydration, hemorrhage, renal dysfunction, etc.).

In an example, the IMD 802 can include one or more traditional cardiac rhythm management (CRM) devices, such as a pacemaker or defibrillator, implanted in a chest of a subject, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the subject 801. In another example, the IMD 802 can include a monitor implanted, for example, subcutaneously in the chest of subject 801.

The IMD 802 can include an assessment circuit configured to detect or determine specific physiologic information of the subject 801, or to determine one or more conditions or provide information or an alert to a user, such as the subject 801 (e.g., a patient), a clinician, or one or more other caregivers. The IMD 802 can alternatively or additionally be configured as a therapeutic device configured to treat one or more medical conditions of the subject 801. The therapy can be delivered to the subject 801 via the lead system and associated electrodes or using one or more other delivery mechanisms. The therapy can include anti-arrhythmic therapy to treat an arrhythmia or to treat or control one or more complications from arrhythmias, such as syncope, congestive heart failure (CHF), or stroke, among others. In other examples, the therapy can include delivery of one or more drugs to the subject 801 using the IMD 802 or one or more of the other ambulatory devices. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF' patients. In some examples, the IMD 802 can include a drug delivery system, such as a drug infusion pump to deliver drugs to the patient for managing arrhythmias or complications from arrhythmias, hypertension, or one or more other physiologic conditions. In yet other examples, the IMD 802 can include a therapy circuit or module configured to treat hypertension (e.g., a neurostimulation therapy circuit, a drug delivery therapy circuit, a stimulation therapy circuit, etc.).

The wearable medical device 803 can include one or more wearable or external medical sensors or devices (e.g., automatic external defibrillators (AEDs), Hotter monitors, patch-based devices, smart watches, smart accessories, wrist- or finger-worn medical devices, such as a finger-based photoplethysmography sensor, etc.). The wearable medical device 803 can include an optical sensor configured to detect a photoplethysmogram (PPG) signal on a wrist, finger, or other location on the subject 801. In other examples, the wearable medical device 803 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 800 can include, among other things: a respiration sensor configured to receive respiration information (e.g., a respiration rate, a respiration volume (tidal volume), etc.); an acceleration sensor (e.g.; an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); or one or more other sensors configured to receive physiologic information of the subject 801.

The external system 805 can include a dedicated hardware/software system, such as a programmer, a remote server-based patient management system, or alternatively a system defined predominantly by software running on a standard personal computer. The external system 805 can manage the subject 801 through the IMD 802 or one or more other ambulatory devices connected to the external system 805 via a communication link 811. In other examples, the IMD 802 can be connected to the wearable device 803, or the wearable device 803 can be connected to the external system 805, via the communication link 811. This can include, for example, programming the IMD 802 to perform one or more of acquiring physiological data, performing at least one self-diagnostic test (such as for a device operational status), analyzing the physiological data to detect a cardiac arrhythmia, or optionally delivering or adjusting a therapy to the subject 801. Additionally, the external system 805 can send information to, or receive information from, the MID 802 or the wearable device 803 via the communication link 811. Examples of the information can include real-time or stored physiological data from the subject 801, diagnostic data, such as detection of cardiac arrhythmias or events of worsening heart failure, responses to therapies delivered to the subject 801, or device operational status of the IMD 802 or the wearable device 803 (e.g.; battery status, lead impedance, etc.). The communication link 811 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards, depending on, in certain examples, the type of devices being connected. Other configurations and combinations of patient data source interfacing are possible.

By way of example and not limitation, the external system 805 can include an external device 806 in proximity of the one or more ambulatory devices, and a remote device 808 in a location relatively distant from the one or more ambulatory devices, in communication with the external device 806 via a communication network 807. Examples of the external device 806 can include a medical device programmer.

The remote device 808 can be configured to evaluate collected subject or patient information and provide alert notifications, among other possible functions. In an example, the remote device 808 can include a centralized server acting as a central hub for collected data storage and analysis. The server can be configured as a uni-, multi-, or distributed computing and processing system. The remote device 808 can receive data from multiple subjects or patients. The data can be collected by the one or more ambulatory devices, among other data acquisition sensors or devices associated with the subject 801. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory devices, such as the MID. By way of example, alert notifications can include a Web page update, phone or pager call, E-mail, SMS, text or "Instant" message, as well as a message to the subject or patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 808 may additionally include one or more locally configured clients or remote clients securely connected over the communication network 807 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 808, including the server and the interconnected clients, may also execute a follow-up scheme by sending follow-up requests to the one or more ambulatory devices, or by sending a message or other communication to the subject 801 (e.g., the patient), clinician or authorized third party as a compliance notification.

The communication network 807 can provide wired or wireless interconnectivity. In an example, the communication network 807 can be based on the Transmission Control Protocol/Internet Protocol (TCP/IP) network communication specification, although other types or combinations of networking implementations are possible. Similarly, other network topologies and arrangements are possible.

One or more of the external device 806 or the remote device 808 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 806 or the remote device 808 can include a respective display unit for displaying the physiological or functional signals, or alerts, alarms, emergency calls, or other forms of warnings to signal the detection of arrhythmias. In some examples, the external system 805 can include an external data processor configured to analyze the physiological or functional signals received by the one or more ambulatory devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory devices or the external system 805 can be implemented using hardware, software, firmware, or combinations thereof. Portions of the one or more ambulatory devices or the external system 805 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals, "Sensors" can include electronic circuits configured to receive information and provide an electronic output representative of such received information.

The patient management system 800 can include a therapy device (e.g., a therapy circuit 809, etc.), such as a drug delivery device configured to provide therapy or therapy information (e.g., dosage information, etc.) to the subject 801, such as using information from one or more of the ambulatory devices. In other examples, one or more of the ambulatory devices can be configured to provide therapy or therapy information to the subject 801. The therapy device can be configured to send information to or receive information from one or more of the ambulatory devices or the external system 805 using the communication link 811. In an example, the one or more ambulatory devices, the external device 806, or the remote device 808 can be configured to control one or more parameters of the therapy device 810.

The external system 805 can allow for programming the one or more ambulatory devices and can receives information about one or more signals acquired by the one or more ambulatory devices, such as can be received via a communication link 811. The external system 805 can include a local external IMD programmer. The external system 805 can include a remote patient management system that can monitor patient status or adjust one or more therapies such as from a remote location.

Figure 9:
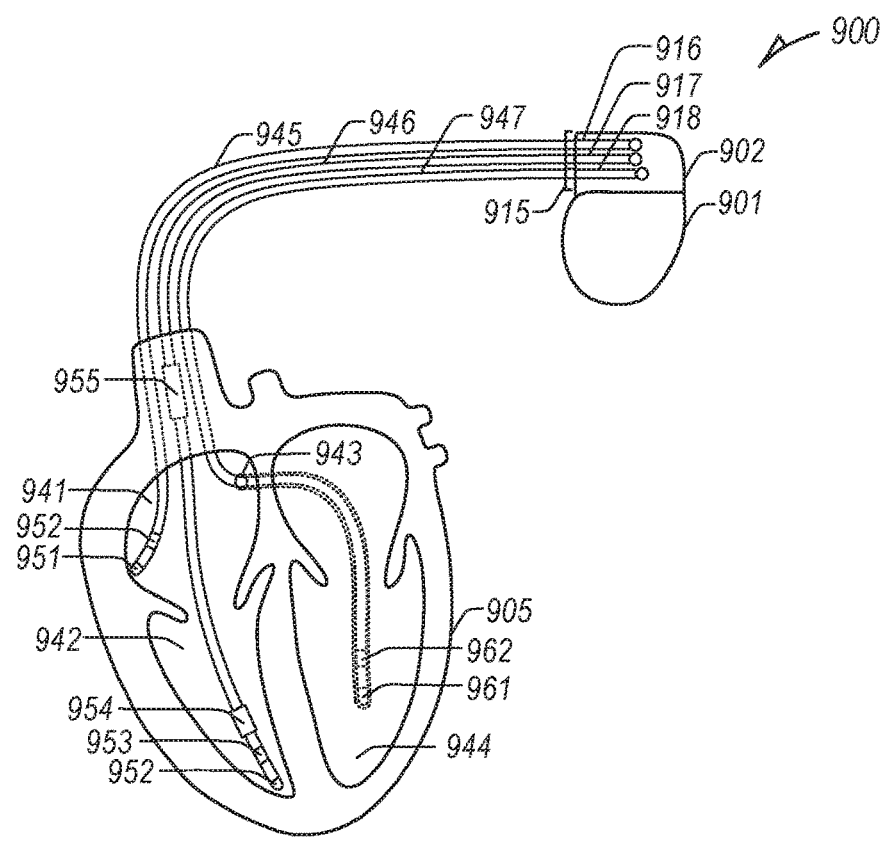
FIG. 9 illustrates an example IMD electrically coupled to a heart using example leads.

FIG. 9 illustrates an example IMD 900 electrically coupled to a heart 905 such as through one or more leads, such as first, second, or third leads 945, 946, 947 coupled to the IMD 900 through lead ports 915, such as first, second, or third lead ports 916, 917, 918 in a header 902 of the IMD 900. In an example, the Imp 900 can include an antenna, such as in the header 902, configured to enable communication with an external system (such as an external system 605 illustrated in FIG. 6).

The IMD 900 may include an implantable cardiac rhythm management (CRM) device, such as a pacemaker, defibrillator, cardiac resynchronizer, or other subcutaneous IMD configured to be implanted in a chest of a subject, having one or more leads to position one or more electrodes or other sensors at various locations in or near the heart 905, such as in one or more of the atria or ventricles. Separate from, or in addition to, the one or more electrodes or other sensors of the leads, the IMD 900 can include one or more electrodes or other sensors (e.g., a pressure sensor, an accelerometer, a gyroscope, a microphone, etc.) powered by a power source in the IMD 900. The one or more electrodes or other sensors of the leads, the IMD 900, or a combination thereof, can be configured detect physiologic information from, or provide one or more therapies or stimulation to, the patient.

Implantable devices can additionally include leadless cardiac pacemakers (LCP), small (e.g., smaller than traditional implantable devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart 905 without traditional lead or implantable device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

The IMD 900 can include one or more monitoring or therapeutic devices such as a subcutaneously implanted device, a wearable external device, a neural stimulator, a drug delivery device, a biological therapy device, or one or more other ambulatory medical devices. The IMD 900 may be coupled to, or may be substituted by a monitoring medical device such as a bedside or other external monitor.

The IMD 900 can include a hermetically sealed housing (CAN) 901 that can house an electronic circuit that can sense a physiologic signal in the heart 905 and can deliver one or more therapeutic electrical pulses to a target region, such as in the heart, such as through one or more leads (e.g., the first, second, and third leads 945, 946, 947). In certain examples, the CRM system 900 can include only a single lead, such as the second lead 946, or can include only two leads, such as the first and second leads 945, 946.

The first lead 945 can include a proximal end that can be configured to be connected to IMD 900 and a distal end that can be configured to be placed at a target location such as in the right atrium (RA) 941 of the heart 905. The first lead 945 can have a first pacing-sensing electrode 951 that can be located at or near its distal end, and a second pacing-sensing electrode 952 that can be located at or near the electrode 951. The electrodes 951 and 952 can be electrically connected to the IMD 900 such as via separate conductors in the first lead 945, such as to allow for sensing of the right atrial activity and optional delivery of atrial pacing pulses. The second lead 946 can be a defibrillation lead that can include a proximal end that can be connected to IMD 900 and a distal end that can be placed at a target location such as in the right ventricle (RV) 942 of heart 905. The second lead 946 can have a first pacing-sensing electrode 952 that can be located at distal end, a second pacing-sensing electrode 953 that can be located near the electrode 952, a first defibrillation coil electrode 954 that can be located near the electrode 953, and a second defibrillation coil electrode 955 that can be located at a distance from the distal end such as for superior vena cava (SVC) placement. The electrodes 952 through 955 can be electrically connected to the IMD 900 such as via separate conductors in the second lead 946. The electrodes 952 and 953 can allow for sensing of a ventricular electrogram and can optionally allow delivery of one or more ventricular pacing pulses, and electrodes 954 and 955 can allow for delivery of one or more ventricular cardioversion/defibrillation pulses. In an example, the second lead 946 can include only three electrodes 952, 954 and 955, The electrodes 952 and 954 can be used for sensing or delivery of one or more ventricular pacing pulses, and the electrodes 954 and 955 can be used for delivery of one or more ventricular cardioversion or defibrillation pulses. The third lead 947 can include a proximal end that can be connected to the MID 900 and a distal end that can be configured to be placed at a target location such as in a left ventricle (LV) 944 of the heart 905. The third lead 947 may be implanted through the coronary sinus 943 and may be placed in a coronary vein over the LV such as to allow for delivery of one or more pacing pulses to the LV. The third lead 947 can include an electrode 961 that can be located at a distal end of the third lead 947 and another electrode 962 that can be located near the electrode 961. The electrodes 961 and 962 can be electrically connected to the IMD 900 such as via separate conductors in the third lead 947 such as to allow for sensing of the LV electrogram and optionally allow delivery of one or more resynchronization pacing pulses from the LV.

The IMD 900 can include an electronic circuit that can sense a physiologic signal. The physiologic signal can include an electrogram or a signal representing mechanical function of the heart 905. The CAN 901 may function as an electrode such as for sensing or pulse delivery. For example, an electrode from one or more of the leads may be used together with the CAN 901 such as for unipolar sensing of an electrogram or for delivering one or more pacing pulses. A defibrillation electrode from the second lead 946 may be used together with the CAN 901 such as for delivering one or more cardioversion/defibrillation pulses. In an example, the IMD 900 can sense impedance such as between electrodes located on one or more of the leads or the CAN 901. The IMD 900 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 900 can be configured to inject current between an electrode on the second lead 946 and the CAN 901, and to sense the resultant voltage between the same electrodes or between a different electrode on the second lead 946 and the CAN 901. A physiologic signal can be sensed from one or more physiologic sensors that can be integrated within the MID 900. The IMD 900 can also be configured to sense a physiologic signal from one or more external physiologic sensors or one or more external electrodes that can be coupled to the MID 900. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

An external system can allow for programming of the IMD 900 and can receives information about one or more signals acquired by IMD 900, such as received via a communication link using an antenna and a telemetry circuit. The external system can include a local external IMD programmer. The external system can include a remote patient management system that can monitor patient status or adjust one or more therapies such as from a remote location.

The communication link can provide for data transmission between the POD 900 and the external system. The transmitted data can include, for example, real-time physiologic data acquired by the IMD 900, physiologic data acquired by and stored in the IMD 900, therapy history data or data indicating MID operational status stored in the IMD 900, one or more programming instructions to the IMD 900 such as to configure the IMD 900 to perform one or more actions that can include physiologic data acquisition such as using programmably specifiable sensing electrodes and configuration, device self-diagnostic test, or delivery of one or more therapies.

Portions of the IMD 900 or the external system can be implemented using hardware, software, or any combination of hardware and software. Portions of the IMD 900 or the external system may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 900, the CRM system 900 can include a subcutaneous medical device (e.g., subcutaneous ICD, subcutaneous diagnostic device), wearable medical devices (e.g., patch-based sensing device), or other external medical devices.

Figure 10:
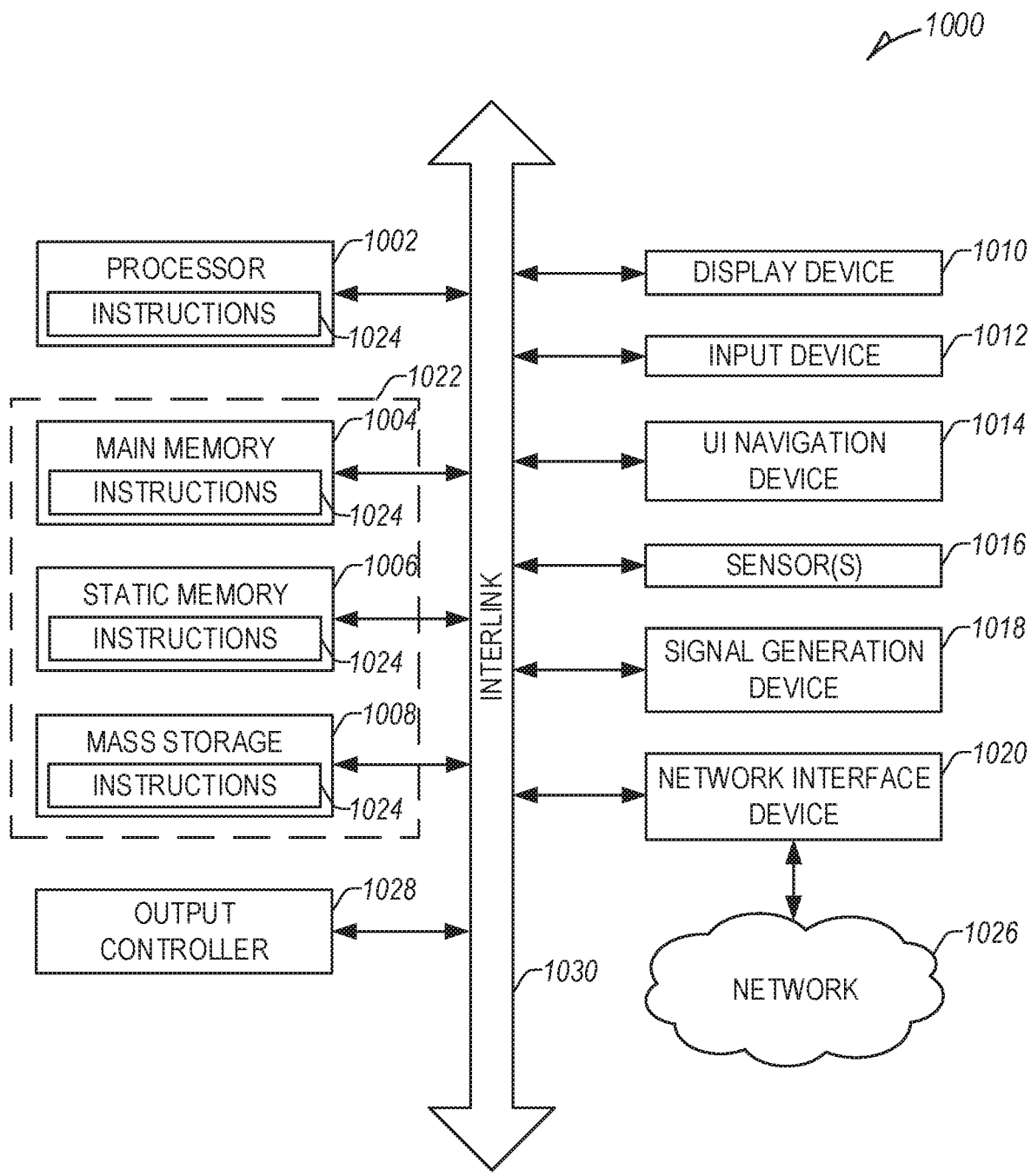
FIG. 10 illustrates a block diagram of an example machine upon which any one or more of the techniques discussed herein may perform.

FIG. 10 illustrates a block diagram of an example machine 1000 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 1000. Circuitry (e.g., processing circuitry) is a collection of circuits implemented in tangible entities of the machine 1000 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry, when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1000 follow.

In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1000 may include a hardware processor 1002 (e.g., a central processing unit (CPU), a graphics processing unit (GPU), a hardware processor core, or any combination thereof), a main memory 1004, a static memory (e.g., memory or storage for firmware, microcode, a basic-input-output (BIOS), unified extensible firmware interface (UEFI), etc.) 1006, and mass storage 1008 (e.g., hard drive, tape drive, flash storage, or other block devices) some or all of which may communicate with each other via an interlink (e.g., bus) 1030. The machine 1000 may further include a display unit 1010, an alphanumeric input device 1012 (e.g., a keyboard), and a user interface (UI) navigation device 1014 (e.g., a mouse). In an example, the display unit 1010, input device 1012, and UI navigation device 1014 may be a touch screen display. The machine 1000 may additionally include a signal generation device 1018 (e.g., a speaker), a network interface device 1020, and one or more sensors 1016, such as a global positioning system (GPS) sensor, compass, accelerometer, or one or more other sensors. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1002, the main memory 1004, the static memory 1006, or the mass storage 1008 may be, or include, a machine-readable medium 1022 on which is stored one or more sets of data structures or instructions 1024 (e.g., software) embodying or utilized by any one or more of the techniques or functions described herein. The instructions 1024 may also reside, completely or at least partially, within any of registers of the processor 1002, the main memory 1004, the static memory 1006, or the mass storage 1008 during execution thereof by the machine 1000. In an example, one or any combination of the hardware processor 1002, the main memory 1004, the static memory 1006, or the mass storage 1008 may constitute the machine-readable medium 1022. While the machine-readable medium 1022 is illustrated as a single medium, the term "machine-readable medium" may include a single medium or multiple media (e.g., a centralized or distributed database, and/or associated caches and servers) configured to store the one or more instructions 1024.

The term "machine-readable medium" may include any medium that is capable of storing, encoding, or carrying instructions for execution by the machine 1000 and that cause the machine 1000 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 may be further transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN); a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIME)), or multiple-input single-output (MISO) techniques. The term "transmission medium" shall be taken to include any intangible medium that is capable of storing, encoding, or carrying instructions for execution by the machine 1000, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. An implantable medical device, comprising:
an implantable housing comprising a conductive surface;
a header coupled to an outer surface of the implantable housing;
control circuitry within the implantable housing, the control circuitry including a telemetry circuit configured to enable radio frequency communication with an external device separate from the implantable medical device; and
a capacitively loaded loop antenna disposed within the header and coupled to the telemetry circuit, the capacitively loaded loop antenna configured to facilitate radio frequency communication comprising a feed, a radiating element, and a return to the conductive surface of the implantable housing, creating an inductance between the feed and the conductive surface,
wherein the feed extends from the conductive surface of the implantable housing, coupling the telemetry circuit to the radiating element through a connector block,
wherein the radiating element comprises a conductor having a major axis with a larger cross section than a cross section of a major axis of the feed and a cross section of a major axis of the return, and a height above a top surface of the implantable housing, creating a capacitance between the radiating element and the conductive surface, wherein the capacitance of the radiating element is configured to counteract the inductance of the capacitively loaded loop antenna, and
wherein the return extends from the radiating element to the conductive surface of the implantable housing, coupling the radiating element to the conductive surface of the implantable housing, wherein the conductive surface of the implantable housing functions as a ground plane for the capacitively loaded loop antenna,
wherein a length, width, and thickness of the radiating element in the header is selected to resonate at a communication frequency between 2.4 and 2.48 GHz when implanted in the body, and
wherein the length of the radiating element is between 5 and 8 mm, the width of the radiating element is between 1 and 2.5 mm, and the thickness of the radiating element is between 0.2 and 0.6 mm.

2. The implantable medical device of claim 1, wherein the capacitively loaded loop antenna has a radiation resistance between 25 and 100 ohms.

3. The implantable medical device of claim 2, wherein the capacitively loaded loop antenna is a 50-ohm antenna.

4. The implantable medical device of claim 1, wherein the capacitance of the radiating element is configured to cancel the inductance of the capacitively loaded loop antenna.

5. The implantable medical device of claim 1, wherein the distance between the feed and the return is selected to provide a radiation resistance of the capacitively loaded loop antenna between 25 and 100 ohms.

6. The implantable medical device of claim 1, wherein the radiating element comprises a planar conductor having a length and width along a top surface of the implantable housing and a thickness normal to the top surface of the implantable housing,
wherein the major axis of the radiating element is along the length of the planar conductor, and
wherein the width of the planar conductor is wider than a width of the feed and the return by at least a factor of two.

7. The implantable medical device of claim 1, wherein the height of the radiating element above the top surface of the implantable housing is between 7 and 11 mm.

8. An implantable medical device, comprising:
an implantable housing;
a header coupled to an outer surface of the implantable housing;
control circuitry within the implantable housing, the control circuitry including a telemetry circuit configured to enable radio frequency communication with an external device separate from the implantable medical device; and
a capacitively loaded loop antenna disposed within the header configured to facilitate radio frequency communication, the capacitively loaded loop antenna comprising a feed, a radiating element, and a return to a conductor of the implantable medical device serving as a ground plane for the capacitively loaded loop antenna, creating an inductance between the feed and the ground plane of the implantable medical device,
wherein the feed is configured to couple the telemetry circuit to the radiating element,
wherein the radiating element comprises a conductor having a length along a major axis with a larger cross section than a cross section of a major axis of the feed and a cross section of a major axis of the return, and a height above the ground plane of the implantable medical device, creating a capacitance between the radiating element and the ground plane, configured to at least partially counter the inductance of the capacitively loaded loop antenna, and
wherein the length of the radiating element is between 5 and 8 mm, the width of the radiating element is between 1 and 2.5 mm, and the thickness of the radiating element is between 0.2 and 0.6 mm.

9. The implantable medical device of claim 8, wherein the implantable housing comprises a conductive surface, the conductive surface comprising the conductor serving as the ground plane of the capacitively loaded loop antenna,
wherein the return extends normal to an upper portion of the conductive surface of the implantable housing, creating the inductance between the feed and the conductive surface, and
wherein the radiating element comprises the height above the top surface of the implantable housing, creating the capacitance between the radiating element and the conductive surface.

10. The implantable medical device of claim 9, wherein the feed extends normal to an upper portion of conductive surface of the implantable housing, coupling the telemetry circuit to the radiating element through a connector block,
wherein the height of the radiating element above the top surface of the implantable housing is between 7 and 11 mm, and
wherein the capacitively loaded loop antenna has a radiation resistance between 25 and 100 ohms.

11. The implantable medical device of claim 8, wherein the telemetry circuit and the capacitively loaded loop antenna are configured to communicate at a desired communication frequency between 2.4 and 2.48 GHz when implanted in the body.

12. The implantable medical device of claim 8, wherein the capacitance of the radiating element is configured to cancel the inductance of the capacitively loaded loop antenna, and
   wherein the distance between the feed and the return is selected to provide a radiation resistance of the capacitively loaded loop antenna between 25 and 100 ohms.

13. The implantable medical device of claim 8, wherein the cross section of the major axis of the radiating element is larger than the major axis of the feed and the major axis of the return by at least a factor of two.

14. The implantable medical device of claim 8, wherein the connector block is located on a side of the implantable housing, perpendicular to the top surface of the implantable housing.

15. The implantable medical device of claim 14, wherein the return extends from the radiating element to the side of the conductive surface of the implantable housing.

16. An implantable medical device, comprising:
   an implantable housing comprising a conductive surface;
   a header coupled to an outer surface of the implantable housing;
   control circuitry within the implantable housing, the control circuitry including a telemetry circuit configured to enable radio frequency communication with an external device separate from the implantable medical device; and
   a capacitively loaded loop antenna disposed within the header and coupled to the telemetry circuit, the capacitively loaded loop antenna configured to facilitate radio frequency communication comprising a feed, a radiating element, and a return to the conductive surface of the implantable housing, creating an inductance between the feed and the conductive surface,
   wherein the feed extends from the conductive surface of the implantable housing, coupling the telemetry circuit to the radiating element through a connector block,
   wherein the radiating element comprises a conductor having a major axis with a larger cross section than a cross section of a major axis of the feed and a cross section of a major axis of the return, and a height above a top surface of the implantable housing, creating a capacitance between the radiating element and the conductive surface, wherein the capacitance of the radiating element is configured to counteract the inductance of the capacitively loaded loop antenna, and
   wherein the return extends from the radiating element to the conductive surface of the implantable housing, coupling the radiating element to the conductive surface of the implantable housing, wherein the conductive surface of the implantable housing functions as a ground plane for the capacitively loaded loop antenna,
   wherein the radiating element comprises a planar conductor having a length and width along a top surface of the implantable housing and a thickness normal to the top surface of the implantable housing,
   wherein the major axis of the radiating element is along the length of the planar conductor, and
   wherein the width of the planar conductor is wider than a width of the feed and the return by at least a factor of two.

17. The implantable medical device of claim 16, wherein the telemetry circuit and the capacitively loaded loop antenna are configured to communicate at a desired communication frequency between 2.4 and 2.48 GHz when implanted in the body.

18. The implantable medical device of claim 16, wherein the capacitance of the radiating element is configured to cancel the inductance of the capacitively loaded loop antenna, and
   wherein the distance between the feed and the return is selected to provide a radiation resistance of the capacitively loaded loop antenna between 25 and 100 ohms.

19. The implantable medical device of claim 16, wherein the connector block is located on a side of the implantable housing, perpendicular to the top surface of the implantable housing.

20. The implantable medical device of claim 19, wherein the return extends from the radiating element to the side of the conductive surface of the implantable housing.

* * * * *